United States Patent [19]

Nagai et al.

[11] Patent Number: 5,111,792
[45] Date of Patent: May 12, 1992

[54] APPARATUS FOR CONTROLLING HEATER FOR OXYGEN SENSOR AND FUEL CONTROL APPARATUS USING THE SAME

[75] Inventors: Toshinari Nagai; Hiroshi Tanaka, both of Susono; Makoto Suzuki, Mishima, all of Japan

[73] Assignee: Toyota Jidosha Kabushiki Kaisha, Toyota, Japan

[21] Appl. No.: 712,120

[22] Filed: Jun. 7, 1991

[51] Int. Cl.$^5$ ............................................. F02M 7/00
[52] U.S. Cl. ................................... 123/440; 123/489
[58] Field of Search ............... 123/440, 489, 424, 406; 204/425, 420, 406, 1 T

[56] References Cited

U.S. PATENT DOCUMENTS

| | | | |
|---|---|---|---|
| 4,655,182 | 4/1987 | Nakano et al. | 123/440 |
| 4,694,809 | 9/1987 | Nakano et al. | 123/489 |
| 4,708,777 | 11/1987 | Kuraoka | 204/1 T |
| 4,715,343 | 12/1987 | Kinoshita | 123/489 |
| 4,721,084 | 1/1988 | Kawarabe et al. | 123/440 |
| 4,721,088 | 1/1988 | Miano et al. | 123/489 |
| 4,915,082 | 4/1990 | Uchinami et al. | 123/489 |
| 4,938,196 | 7/1990 | Hashi et al. | 123/489 |

FOREIGN PATENT DOCUMENTS

| | | | |
|---|---|---|---|
| 197459 | 12/1982 | Japan | 123/489 |
| 164240 | 8/1985 | Japan | 123/489 |

Primary Examiner—Raymond A. Nelli
Attorney, Agent, or Firm—Kenyon & Kenyon

[57] ABSTRACT

An apparatus for controlling a heater for an oxygen sensor which includes a heater resistance value detecting unit for detecting a heater resistance value of the heater, the power control unit for controlling a power supplied to the heater so that the heater resistance value is equal to a target resistance value, and a target resistance value setting unit for calculating a rate of change in the heater resistance value of the heater measured by the heater resistance value detecting unit, and for determining the target resistance value on the basis of the rate of change in the heater resistance value.

17 Claims, 13 Drawing Sheets

APPARATUS FOR CONTROLLING HEATER FOR OXYGEN SENSOR AND FUEL CONTROL APPARATUS USING THE SAME

BACKGROUND OF THE INVENTION (1) Field of the Invention

The present invention generally relates to an apparatus for controlling a heater for an oxygen sensor, and more particularly to a heater control apparatus for varying electrical power supplied to a heater provided in an oxygen sensor fastened to an exhaust gas passage of an internal combustion engine so that the resistance value of the heater becomes equal to a target resistance value. The present invention is further concerned with a fuel control apparatus using such an apparatus for controlling the heater.

(2) Description of the Related Art

Recently, various control devices have been developed which are directed to an improvement in the output power in an internal combustion engine, a reduction of fuel consumption or a reduction of undesirable exhaust gases. Such control devices employ oxygen sensors. As is well known, an oxygen sensor can be used for measuring the concentration of an oxygen component contained in the exhaust gas. An oxygen sensor has a sensor element (sense portion) formed of a solid electrolyte or a semiconductor. An output signal of the oxygen sensor depends on the temperature of the sensor element thereof.

The oxygen sensor is equipped with a heater in order to make the sensor element operate effectively under a condition where the temperature of the exhaust gas is low and to stably maintain the temperature of the sensor element. Generally, the electric resistance of a metallic material is based on the temperature thereof. Thus, it is possible to maintain the metallic material at a constant temperature by maintaining the resistance thereof at a constant value. From the above point of view, the heater resistance of the heater is controlled by adjusting power supplied to the heater so that the heater resistance is maintained at a target resistance value (see Japanese Laid-Open Patent Publication No. 57-197459).

An internal combustion engine is controlled by a feedback control system using the oxygen sensor. A predetermined timing of fuel injection is adjusted based on the concentration of oxygen contained in, the exhaust gas detected by the oxygen sensor so that the mixture entering drawn into a cylinder has a target air-fuel ratio, such as a stoichiometric air-fuel ratio. In such a feedback control system, it is necessary to learn (calibrate) the heater resistance and correct for measurement error which are dependent on the electrical characteristics of the oxygen sensor.

For the above-mentioned purpose, Japanese Laid-Open Patent Publication No. 60-164240 discloses the following heater control apparatus. The temperature of inlet air and the temperature of a coolant are measured. It is recognized that the internal combustion engine is cooled when the inlet air temperature is almost the same as the coolant temperature. Since the heater of the oxygen sensor and the coolant are in a state of equilibrium, the temperature of the coolant can be considered to be the temperature of the heater of the oxygen sensor. The heater resistance obtained at 0° K. is calculated, so that differences between the characteristics of the oxygen sensors can be compensated for.

The heater control apparatus disclosed in Japanese Laid-Open Patent Publication No. 60-164240 is based on the fact that the characteristics of different oxygen sensors vary differently with temperature. Referring to FIG. 1, lines I and II relate to two different oxygen sensors, and RH1 and RH2 denote heater resistance values obtained when the air-fuel ratio (A/F) is equal to a stoichiometric air-fuel ratio. It will be seen from the graph of FIG. 1 that the difference between the heater resistances given by the two lines I and II vary with sensor (heater) temperature. More specifically, the difference between the lines I and II increases as the sensor temperature increases. The above-mentioned conventional heater control apparatus does not take into account the fact shown in FIG. 1. Thus, the characteristic differences of oxygen sensors cannot be compensated for effectively, and an erroneous calibration of the heater resistance is carried out. As a result, the heater temperature is regulated at a temperature which deviates from the target temperature, and the air-fuel ratio deviates from the target air-fuel ratio. This degrades emissions.

SUMMARY OF THE INVENTION

It is a general object of the present invention to provide an apparatus for controlling a heater for an oxygen sensor in which the above-mentioned disadvantages are eliminated.

A more specific object of the present invention is to provide a heater control apparatus capable of more precisely controlling the oxygen sensor.

The above objects of the present invention are achieved by an apparatus for controlling a heater for an oxygen sensor, the apparatus comprising: a heater resistance value detecting unit for detecting a heater resistance value of the heater; a power control unit, operatively coupled to the heater and the heater resistance value detecting unit, for controlling the power supplied to the heater so that the heater resistance value is equal to a target resistance value; and a target resistance value setting unit, operatively coupled to the heater resistance value detecting unit and the power control unit, for calculating a rate of change in the heater resistance value of the heater measured by the heater resistance value detecting unit, and for determining the target resistance value on the basis of the rate of change in the heater resistance value.

Another object of the present invention is to provide a fuel control apparatus using the above-mentioned heater control apparatus.

This object of the present invention is achieved by an apparatus for controlling an amount of fuel supplied to an internal combustion engine on the basis of the concentration of oxygen contained in the exhaust gas of the internal combustion engine, the apparatus comprising: a fuel injection unit for injecting fuel into the internal combustion engine; an oxygen sensor for measuring the concentration of oxygen contained in the exhaust gas; a heater for heating the oxygen sensor; and a control unit, operatively coupled to the fuel injection unit, for controlling the amount of fuel injected by the fuel injection unit on the basis of the concentration of oxygen measured by the oxygen sensor. The control unit includes the aforementioned heater control apparatus.

BRIEF DESCRIPTION OF THE DRAWINGS

Other objects, features and advantages of the present invention will become more apparent from the following detailed description when read in conjunction with the accompanying drawings, in which.

DESCRIPTION OF THE PREFERRED EMBODIMENTS

Figure 2:
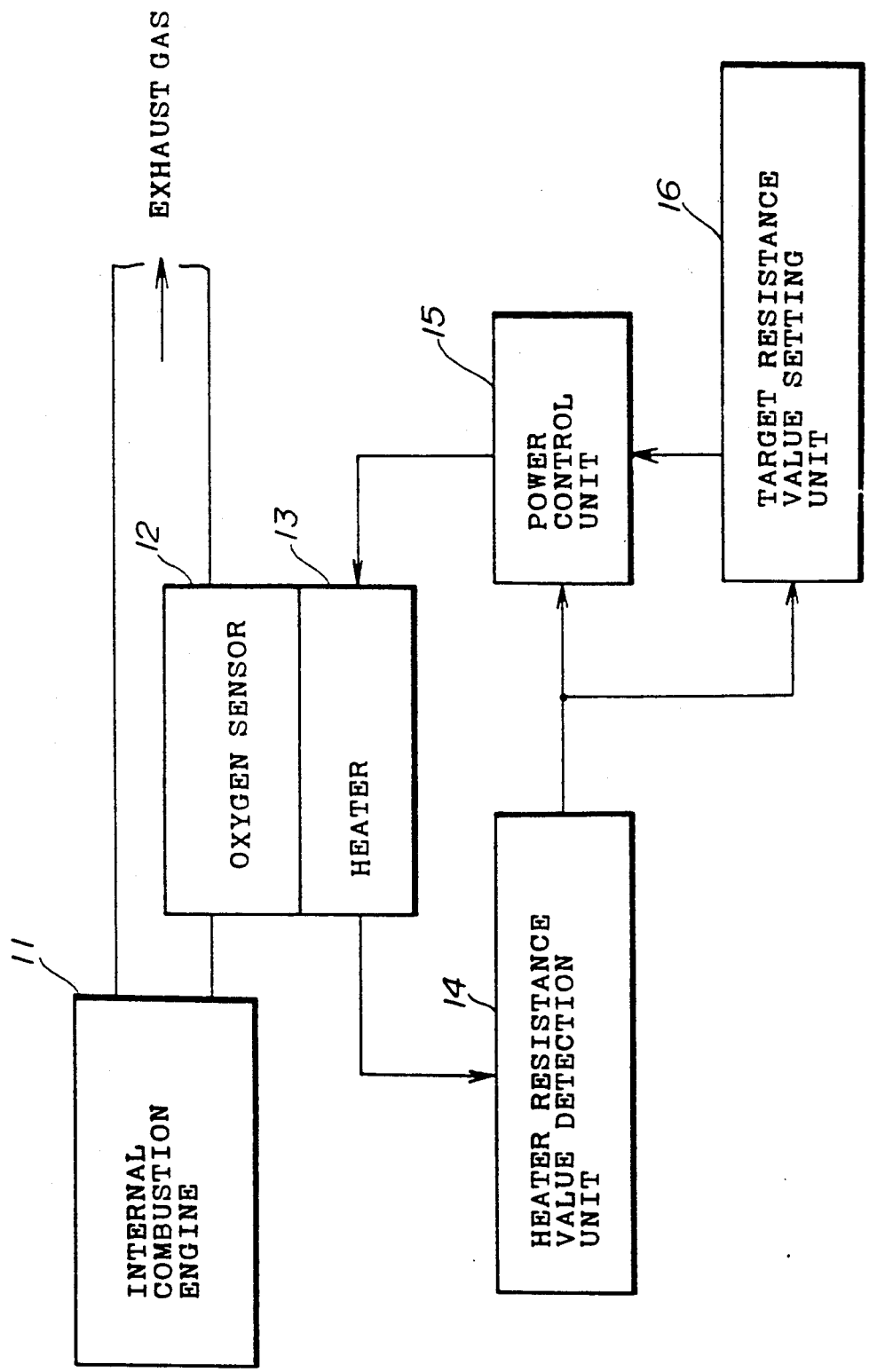
FIG. 2 is a block diagram of an outline of a heater control apparatus according to the present invention.

FIG. 2 shows an outline of an apparatus for controlling a heater for an oxygen sensor according to the present invention. The apparatus includes a heater resistance value detection unit 14, a power control unit 15 and a target resistance value setting unit 16. An oxygen sensor 12 is fastened to an exhaust gas passage extending from an internal combustion engine 11, and is equipped with a heater 13. The heater resistance value detection unit 14 detects the resistance value of the heater 13. The power control unit 15 controls power supplied to the heater 13 so that the resistance value of the heater 13 always converges to a target resistance value. The target resistance value setting unit 16 outputs a predetermined target resistance value to the power control unit 15 when the engine 11 is started so that a predetermined amount of power is supplied to the heater 13. During this time, the target resistance value setting unit 16 calculates a time rate of change of the heater resistance, and determines an appropriate target resistance value on the basis of the time rate of change of the heater resistance. When the engine 11 is started, there is little change in the temperature of the exhaust gas. Thus, the temperature in the vicinity of the oxygen sensor 12 does not change greatly. Further, most of energy which changes the heater resistance is the power supplied to the heater 13. Thus, the oxygen sensor 12 is little affected by the temperature in the vicinity thereof.

Figure 3:
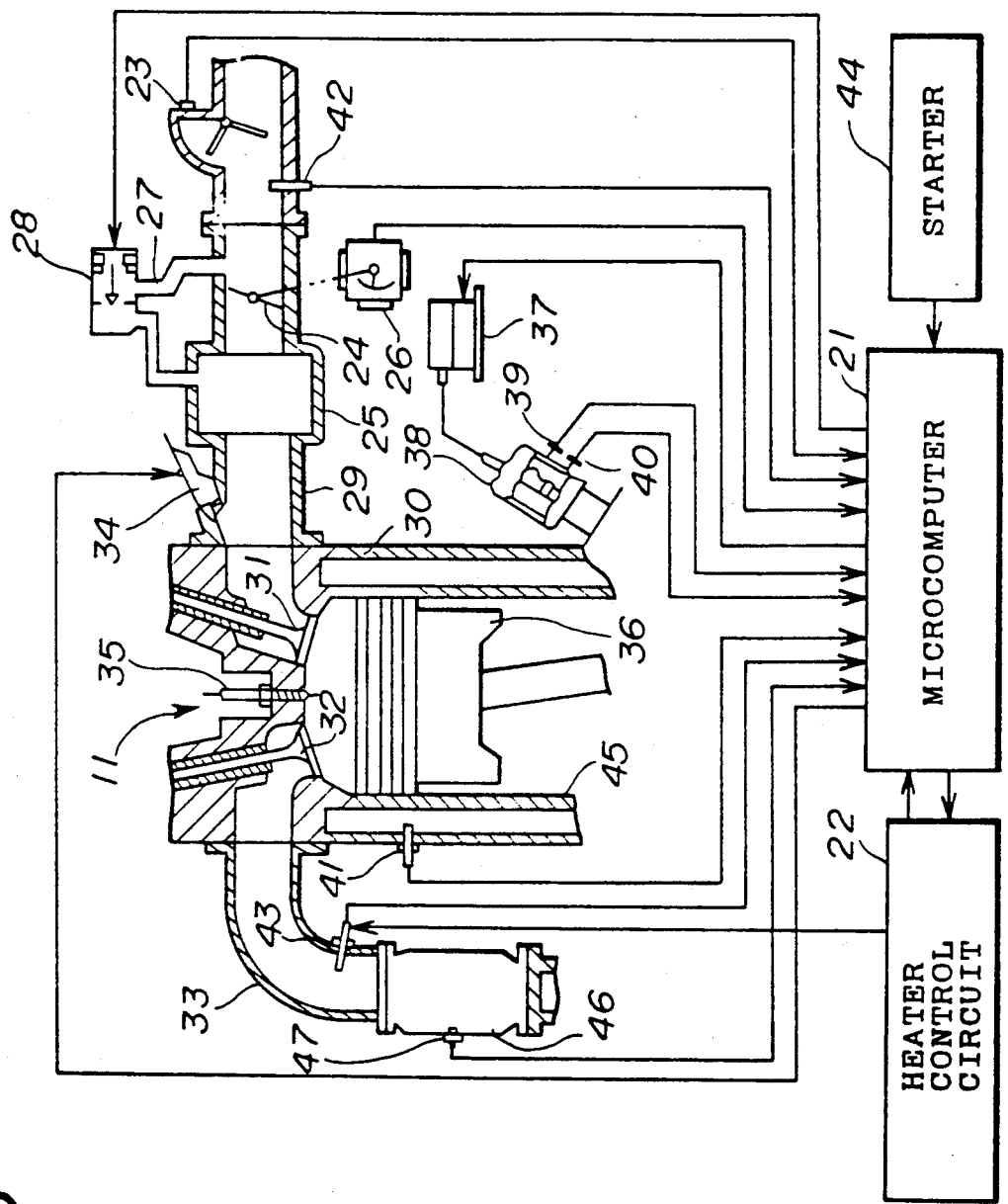
FIG. 3 is a diagram showing an internal combustion engine which uses a heater control apparatus according to an embodiment of the present invention.

FIG. 3 shows an internal combustion engine to which a preferred embodiment of the present invention is applied. The internal combustion engine shown in FIG. 3, which corresponds to the internal combustion engine shown in FIG. 2, is for use in an automobile vehicle. The entire operation of the internal combustion engine 11 shown in FIG. 3 is controlled by a microcomputer 21. The heater resistance value detection unit 14 and the power control unit 15 shown in FIG. 2 are realized by a heater control circuit 22 and a software operation of the microcomputer 21. The target resistance value setting unit 16 shown in FIG. 2 is realized by the software operation of the microcomputer 21.

An air flow meter 23 is provided in an intake air passage. A throttle valve 24 is provided on the downstream side of the air flow meter 23. A surge tank 25 is provided on the downstream side of the throttle valve 24. A throttle position sensor 26 is fastened to a throttle body, and detects the motion of the throttle value 24 by means of a plurality of built-in contacts. When the throttle valve 24 is completely closed (that is, positioned at an idle position), an IDL contact of the throttle position sensor 26 is turned ON. A bypass passage 27 bypasses the throttle valve 24 and connects the downstream side of the air flow meter 23 and the surge tank 25. An idle speed control valve (ISCV) 28 is provided for in the bypass passage 27, and controls the amount of air passing through the bypass passage 27.

The surge tank 25 is coupled to a combustion chamber 30 of the engine via an intake manifold 29. A suction or inlet valve 31 and an exhaust value 32 are provided in the combustion chamber 30, which is coupled to an exhaust manifold 33. A fuel injection valve 34 injects fuel into air passing through the intake manifold 29. An ignition plug 35 is provided so that a part thereof projects into the combustion chamber 30. A piston 36 reciprocates in a cylinder. An ignitor 37 generates a high voltage. A distributor 38 distributes the high voltage generated by the ignitor 37 to plugs 35 mounted on top of the cylinders.

The engine is provided with various sensors including a cylinder discrimination sensor 38, a turning angle sensor 40, a water temperature sensor 41, an intake air temperature sensor 42, an oxygen sensor 43 with a heater 43a (FIG. 6), and a starter 44. Detection signals output by these sensors are input to the microcomputer 21.

The cylinder discrimination sensor 39 generates a predetermined number of pulses synchronized with the rotation of a shaft of the distributor 38. Such a predetermined number of pulses serves as a cylinder discrimination signal. The turning angle sensor 40 detects the rotation of the shaft of the distributor 38, and measures the revolution of the engine (engine speed). The water temperature sensor 41 is provided so that it penetrates an engine block 45, and partially projects in a water jacket, and measures the temperature of coolant. The intake air sensor 42 measures the temperature of the intake air on the downstream side of the air flow meter 23. The starter 44 detects the fact that the engine is being started (in the cranking state), and outputs a detection signal indicative of the cranking state. The oxygen sensor 43 is disposed so that a part thereof projects in the exhaust manifold 33, and measures the concentration of oxygen contained in the exhaust gas before it enters into a three-way catalyst 46. An exhaust gas temperature sensor 47, which is provided for in the three-way catalyst 46, measures the temperature thereof.

The oxygen sensor 43 with the heater 43a (FIG. 6) includes, for example, an oxide semiconductor (corresponding to the oxygen sensor 12 shown in FIG. 2) containing titania ($TiO_2$) in the form of a film on the surface of an insulator base containing alumina, and the heater 43a for heating the titania film. The resistance of titania changes in accordance with the concentration of oxygen contained in the exhaust gas which is in contact with the titania film. Thus, it is possible to measure the concentration of oxygen by detecting a change in the resistance value of titania.

Figure 4:
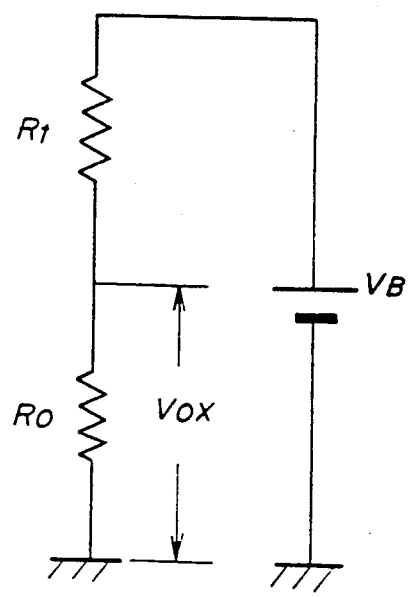
FIG. 4 is an equivalent circuit diagram of an oxygen sensor.

FIG. 4 is an equivalent circuit of the titania $O_2$ sensor. $R_t$ is the resistance value of titania, which changes based on the oxygen concentration. A resistor $R_0$ is connected in series, and a voltage $V_B$ is applied across a series circuit consisting of the resistors $R_0$ and $R_t$.

Figure 5:
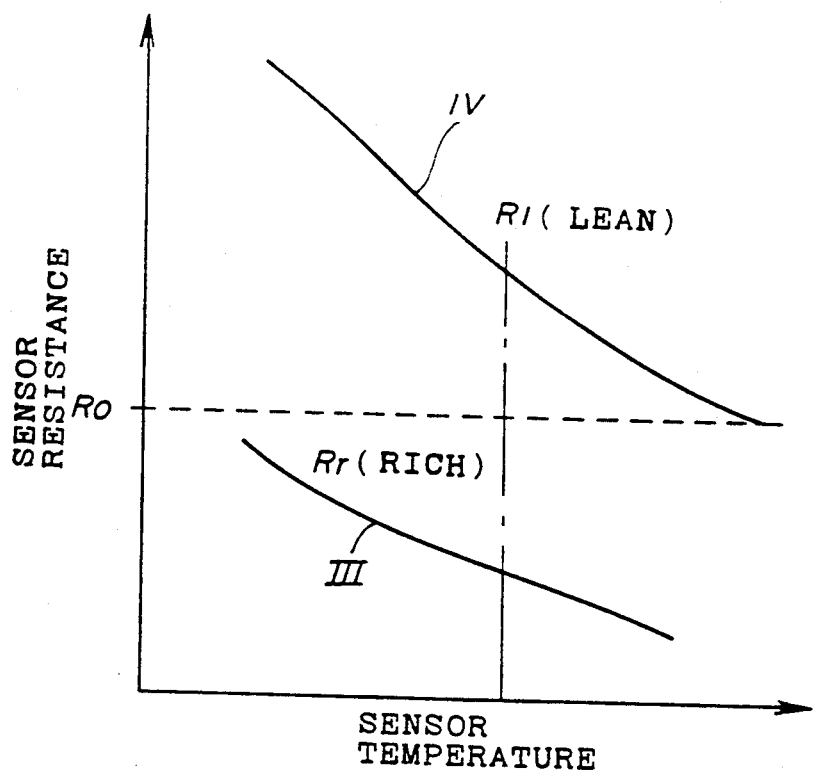
FIG. 5 is a graph showing a relationship between the resistance of the oxygen sensor and the temperature thereof.

Referring to FIG. 5, the resistance $R_t$ of titania has a low-resistance characteristic, as shown by curve III, when the oxygen concentration is low, that is, when the air-fuel ratio is rich. On the other hand, when the air-fuel ratio is lean, the resistance $R_t$ of titania has a high-resistance characteristic, as shown by curve IV. A change in the resistance $R_t$ of titania is not detected directly, but detected, as shown in FIG. 4. More specifically, the resistance $R_t$ is detected by detecting a divided voltage (detection voltage $V_{OX}$ developed across the resistor $R_0$. When the air-fuel ratio is rich, the detection voltage $V_{OX}$ is larger than that obtained when the air-fuel ratio is lean.

The detection voltage $V_{OX}$ is expressed as follows:

$$V_{OX} = V_B \cdot R_0/(R_0 + R_t) \quad (1)$$

Thus, with a suitable value of $R_0$, $R_t << R_0$ when the air-fuel ratio is rich, and thus the following equation is obtained:

$$V_{OX} = V_B \text{ (high (H) level)}.$$

On the other hand, when the air-fuel ratio is lean, $R_t >> R_0$, and thus the following equation is obtained:

$$V_{OX} = 0 \text{ (}V\text{) (low (L) level)}.$$

As can be seen from FIG. 5, the resistance $R_t$ of titania depends on not only the oxygen concentration but also the temperature of titania itself (sensor temperature). Thus, it is necessary to accurately control the temperature of the oxygen sensor so that it is equal to an appropriate temperature. For the above-mentioned reason, a heater for heating titania is provided in the oxygen sensor. Further, based on the fact that the resistance of the heater is associated with the sensor temperature, the power supplied to the heater is controlled so that the heater resistance is equal to the target resistance value. In this way, the temperature of the oxygen sensor is controlled to a desired temperature.

Figure 6:
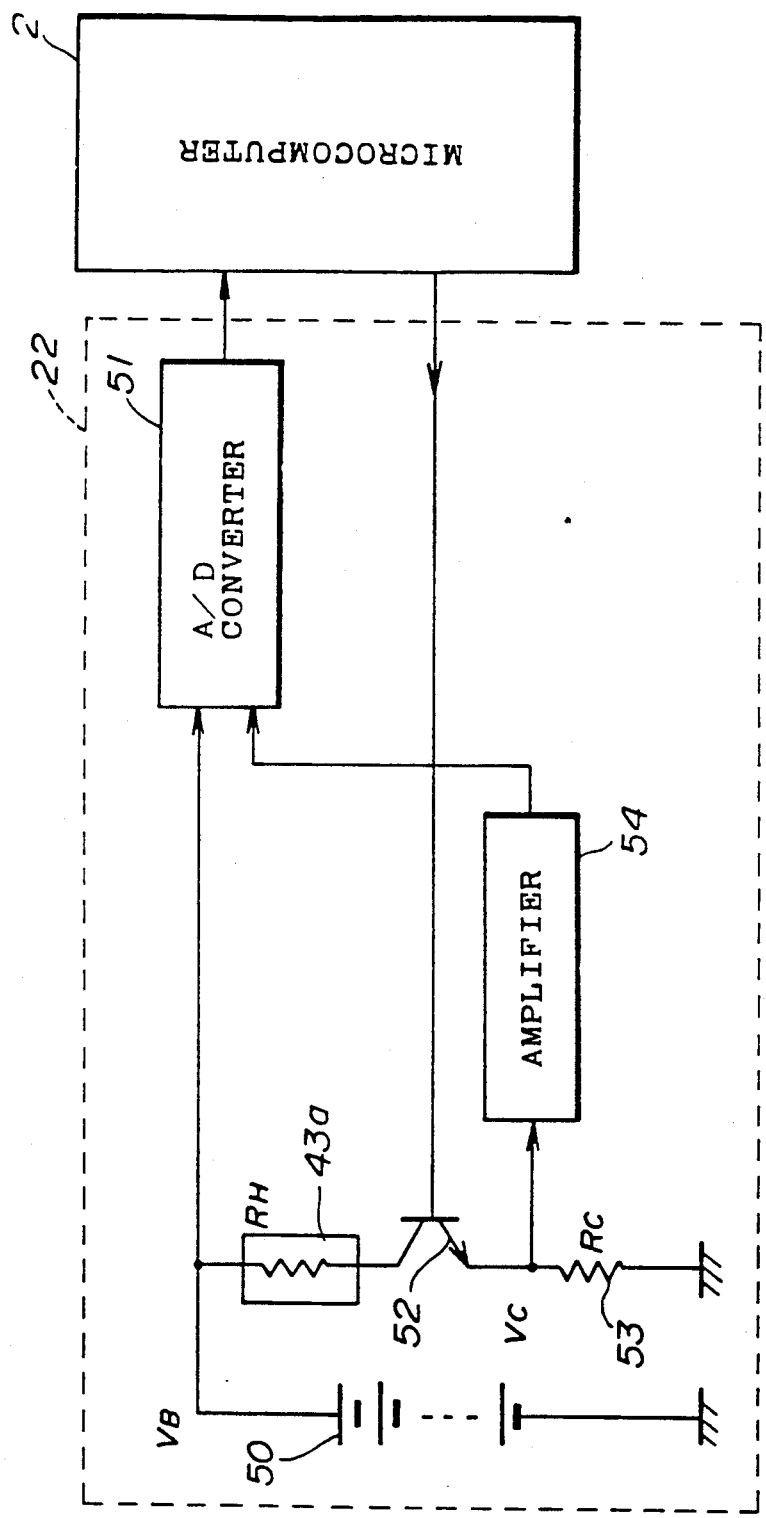
FIG. 6 is a block diagram of a heater control circuit used in the internal combustion engine shown in FIG. 3.

The power supplied to the heater 43a in the oxygen sensor 43 is controlled by a pulse signal generated by the heater control circuit 22. FIG. 6 is a circuit diagram of the heater control circuit 22. As shown in FIG. 6, the heater control circuit 22 has a battery 50, an analog-to-digital (A/D) converter 51, a switching transistor 52, a resistor 53 and an amplifier 54. The voltage $V_B$ of the battery 50 is applied to the heater 43a provided for in the oxygen sensor 43, and is converted into a digital signal input to the microcomputer 21 as an operation power supply voltage. The resistance RH of the heater 43a changes based on the temperature of the heater 43a. The other end of the heater 43a is coupled to one end of the resistor 53 via the collector and emitter of the switching transistor 52. The other end of the resistor 53 is grounded. The resistor 53 has a resistance $R_C$. The amplifier 54 amplifies a voltage $V_C$ obtained at the one end of the resistor 53, and outputs an amplified voltage to the A/D converter 51. A pulse signal generated by the microcomputer 21 is applied to the base of the switching transistor 52, so that it is turned ON/OFF and thus the power supplied to the heater 43a is controlled.

Figure 7:
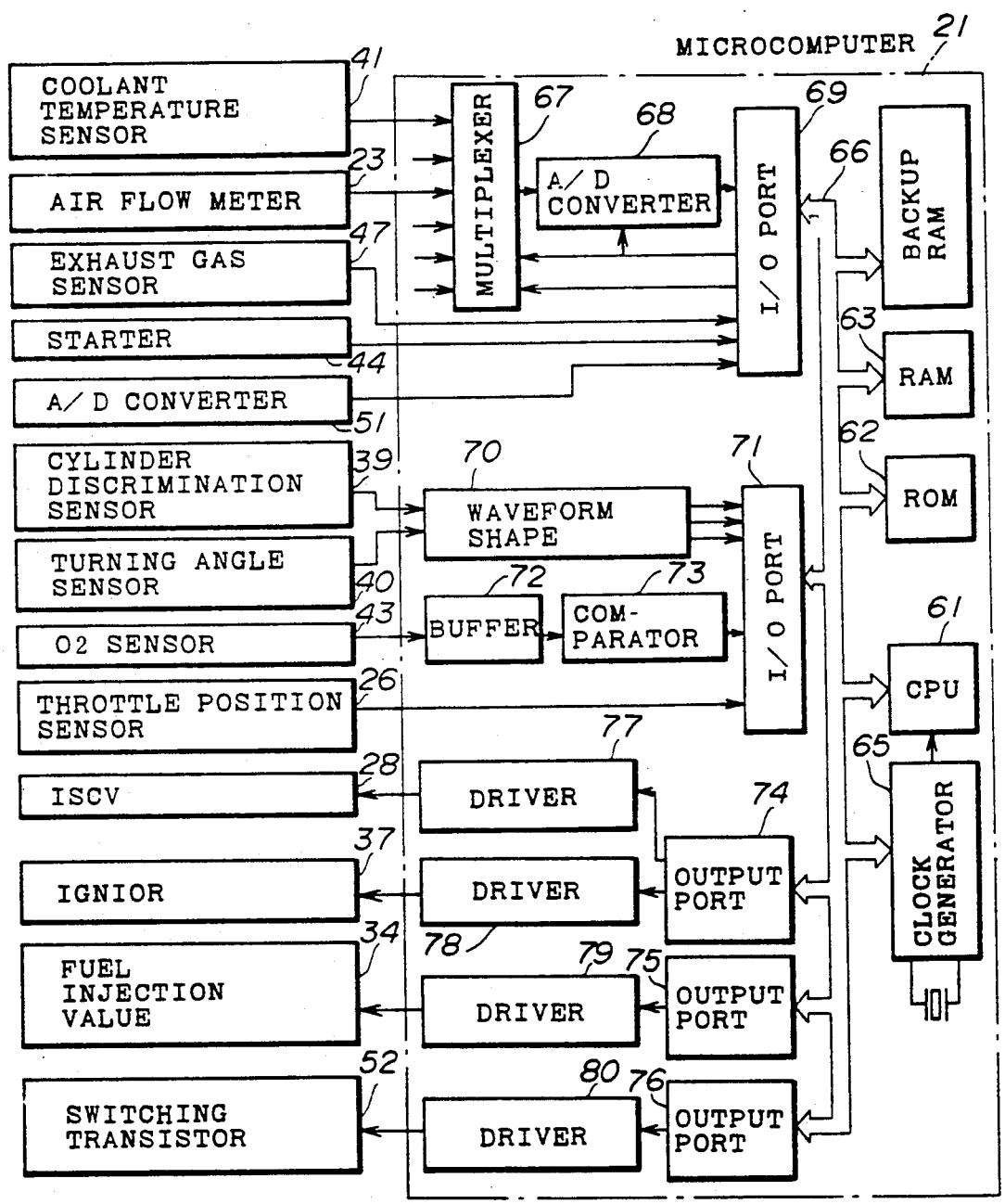
FIG. 7 is a block diagram of a microcomputer used in the internal combustion engine shown in FIG. 3.

A description will now be given of a hardware structure of the microcomputer 21 with reference to FIG. 7, in which those parts which are the same as those shown in FIGS. 3 and 6 are given the same reference numerals. The microcomputer 21 includes a central processing unit (CPU) 61, a read only memory (ROM) 62, a random access memory (RAM) 63, a backup RAM 64 and a clock generator 65. These structural elements are coupled to each other via a bidirectional bus 66. The CPU 61 controls the entire operation of the microcomputer 21. The ROM 62 stores programs executed by the CPU 61. The RAM 63 is used as a work area of the CPU 61. The backup RAM 64 stores data after the engine is turned OFF. The clock generator 65 generates clocks including a master clock supplied to the CPU 61.

The detection signals from the water temperature sensor 41 and the air flow meter 23 are transferred to the bus line via a multiplexer 67, an A/D converter 68 and an input/output port 69. The detection signals from the starter 44 and the exhaust gas temperature sensor 47 as well as a digital signal from the A/D converter 51 are transferred to the bus 66 via the input/output port 69. The cylinder discrimination signal from the cylinder discrimination sensor 39 and an engine speed signal from the turning angle sensor 40 are transferred to the bus 66 via a waveform shaping circuit 70 and an input/output port 71. The detection signal of the oxygen sensor 43 passes through a buffer 72 and a comparator 73, and is transferred, together with the signal from the throttle position sensor 26, to the bus 66 via the input/output port 71.

Control signals generated by the CPU 61 are input to output ports 74, 75 and 76 via the bus 66. The control signals from the output port 74 are input to driver circuits 77 and 78, and input to the idle speed control valve (ISCV) 28 and the ignitor 37, respectively. The control signal from the output port 75 is supplied to the fuel injection value 34 via the driver circuit 79. The control signal from the output port 76 is supplied to the switching transistor 52 via the driver circuit 80.

Figure 8:
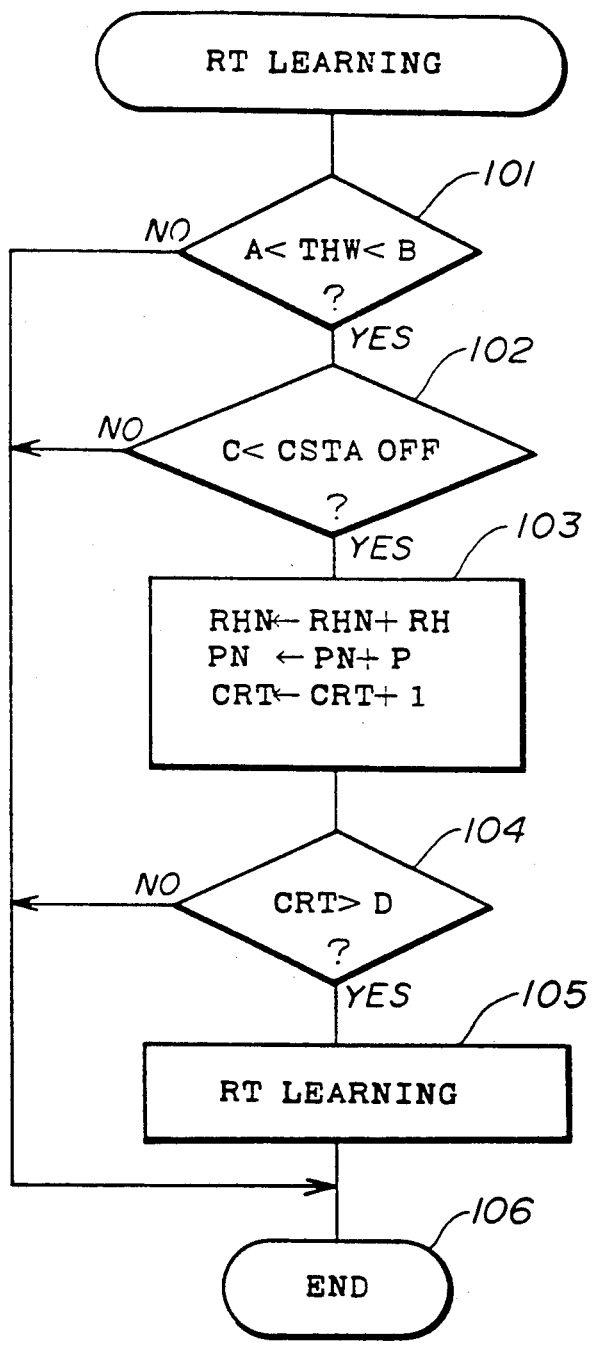
FIG. 8 is a flowchart of a target resistance value learning routine executed under the control of a central processing unit provided in the microcomputer shown in FIG. 7.

A description will now be given of a control procedure for a heater executed under the control of the microcomputer 21. FIG. 8 is a flowchart of an operation (named RT learning (calibration) routine) which realizes the target resistance value setting unit 16 shown in FIG. 2. The RT learning routine shown in FIG. 8 is activated at intervals equal to, for example, a few milliseconds to one second. At step 101, the CPU 61 determines, on the basis of the detection signal from the water temperature sensor 41, whether or not the temperature of the coolant, now labeled THW, is between A°B and B°C (for example, between −15° C. and, +50° C.). This avoids execution of the RT learning routine when there is a disruptive influence of the temperature on the heater 43a when the coolant is lower than temperature A°C or higher than B° C. That is, if the learning determination of the target resistance value is based on the power supplied to the heater 43a in a state where the engine is in the idle state, the temperature of the exhaust gas obtained in the vicinity of the oxygen sensor 43 is between approximately 150° and 500° C., depending on the driving condition before the idle state (for example, the vehicle may have been traveling with a large load). On the other hand, at the time of cold start where A<THW<B is satisfied, the exhaust gas temperature obtained in the vicinity of the oxygen sensor 43 is about −15° C. before the engine starts to rotate, and has increased to about +50° C. when the RT learning routine ends after the engine starts.

The upper limit temperature B°C, used at step 101 for determining whether or not the RT learning routine should be started, is a temperature obtained during a step in which the engine 11 becomes cooler by stopping engine 11 after it has been warmed up. The temperature obtained in the vicinity of the oxygen sensor 43 (particularly, sensor element) is already equal to the atmospheric temperature. In this way, when A<THW<B is satisfied, there are slight variations in conditions obtained before the RT learning routine is carried out. The RT learning routine is intended to detect variations in the resistance of the heater 43a introduced during the production process thereof and to correct the heater resistance so that it becomes equal to the target resistance value. Thus, it is preferable that the temperature obtained in the vicinity of the oxygen sensor 43 be within a predetermined range while the RT learning routine is being carried out.

The condition defined at step 101 means that the RT learning routine is little affected by the temperature obtained in the vicinity of the oxygen sensor 43 since variations in the heater resistance obtained during the RT learning routine is much more dependent on the power supplied to the heater 43a. More specifically, in the idle state, the temperature of the oxygen sensor 43 obtained during the RT learning routine is between approximately 600° C. and 850° C. when the heater resistance is controlled to become equal to the target resistance value. On the other hand, when the heater resistance is controlled under the condition defined at step 101, the temperature of the oxygen sensor 43 is between about −10° C. and 200° C. It can be seen from the above that the ratio of power supplied to the heater 43a to all energy which causes a variation in the resistance of the heater 43a, when the condition defined at step 101 is satisfied, is greater than that obtained when the engine 11 is in the idle state. Further, as has been described previously, the temperature in the vicinity of the oxygen sensor 43 obtained at the time of the cold start does not vary greatly.

When the starter 44 is turned OFF after the starter 44 turns ON in the state where the condition defined at step 101 is satisfied (cold start), a counter value, labeled CSTAOFF, starts to increase its counter value at a predetermined rate. At step 102, the CPU 61 determines whether or not the counter value CSTAOFF is larger than a predetermined value C. During the cranking or during a predetermined time immediately after the cranking ends, the counter value CSTAOFF is smaller than the predetermined value C. In this state, the battery voltage drops greatly, and thus the average amount (PN) of the power supplied to the heater 43a (hereinafter referred to as an average power PN) decreases. That is, if the battery voltage ($V_B$ shown in FIG. 6) can be definitely obtained, it is desired that the learning routine be carried out as soon as possible from the time when the starter 44 is turned OFF. This is because stable variations in the resistance of the heater 43 are obtained when the temperature obtained in the vicinity of the oxygen sensor 43 is low. However, the A/D converter 51 (FIG. 6) operates on the basis of the real battery voltage which is smaller than that assumed by the heater control routine. Thus, the real battery voltage is much smaller than the battery voltage $V_B$ when the engine is rotating at a certain speed soon after the starter 44 has been turned OFF. The power supplied to the heater 43a now labeled P is defined as follows:

$$P = BATCOR \times IHT - IHT \times IHT \times K \qquad (2)$$

where BATCOR is the battery voltage obtained after correction, IHT is the heater current passing through the heater 43a, and K is a coefficient. Thus, if the after-correction battery voltage BATCOR has an error, the average power PN calculated at step 103 will have an error. In order to avoid the above-mentioned problem, step 102 detects the state where the engine speed Ne and the heater battery voltage $V_B$ can be definitely detected, after the starter 44 is changed from ON to OFF.

Figure 9:
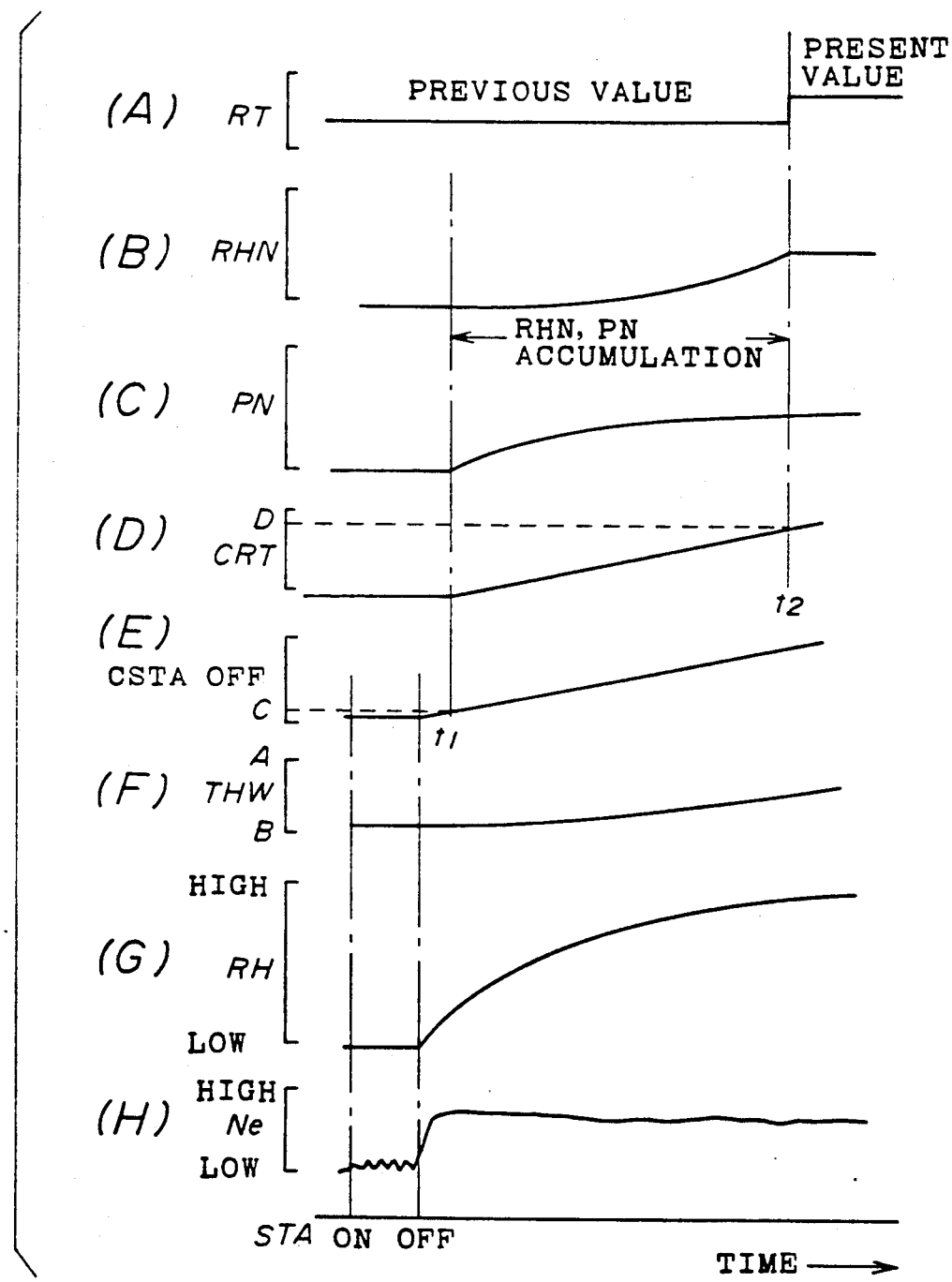
FIG. 9 is a waveform diagram showing the operation of the embodiment of the present invention.

FIG. 9(E) shows the counter value CSTAOFF, which becomes larger than the predetermined value C at time $t_1$ after the starter 44 is turned OFF. At this time, the engine speed Ne is already stable, as shown in FIG. 9(H). Further, at time $t_1$, the coolant temperature THW is between A°C and B°C, as shown in FIG. 9(F).

When C<CSTAOFF is satisfied at step 102, the CPU 61 executes step 103, at which step an accumulated value RHN of the heater resistance values RH of the oxygen sensor 43 is calculated by the following formula:

$$RHN \leftarrow RHN + RH \qquad (3).$$

Further, the average energy (accumulated power) PN of the power P supplied to the heater 43a is calculated as follows:

$$PN \leftarrow PN + P \qquad (4).$$

Moreover, an accumulation counter value CRT is incremented by 1. FIG. 9(B) shows a change in the accumulated value RHN of the heater resistance values RH, FIG. 9(C) shows a change in the average energy PN, and FIG. 9(G) shows a change in the heater resistance value RH.

Figure 10:
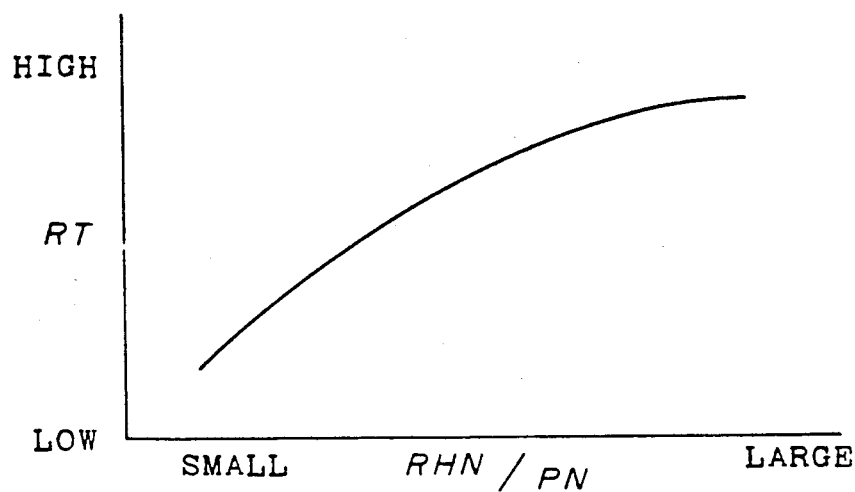
FIG. 10 is a graph showing a relationship between the target resistance value and a ratio of an accumulated value of heater resistance values to an average energy supplied to the heater.

After executing step 103, the CPU 61 executes step 104, at which step it is determined whether the accumulated counter value CRT obtained at step 103 is greater than a predetermined value D (for example, between 5 and 100). When CRT≧D, the CPU 61 ends the RT learning routine, which will occur after a predetermined time. In the above-mentioned way, the steps 101-104 are repeatedly carried out. When the accumulated counter value CRT exceeds the predetermined value D at time $t_2$, as shown in FIG. 9(D), the CPU 61 executes step 105, at which step the target resistance value RT is determined, by using a map (table) defining a curve shown in FIG. 10, on the basis of a ratio of the accumulated heater resistance value RHN during the predetermined period to the average energy PN related thereto (RHN/PN). FIG. 10 shows the relationship between the target resistance value RT determined by the procedure shown in FIG. 8 and the ratio RHN/PN. After the target resistance value RT is determined (revised) at step 105, the RT learning routine ends.

As has been described above, there is a high correlation between the power P supplied to the heater 43a and the heater resistance value RH in the state where there is little influence by the temperature in the vicinity of the oxygen sensor 43 (in other words, the state where there is a great influence of the heater 43a). With the above in mind, the target resistance value RT is obtained by the RT learning routine using the ratio RHN/PN, so that variations in the heater resistance can be detected.

Figure 1:
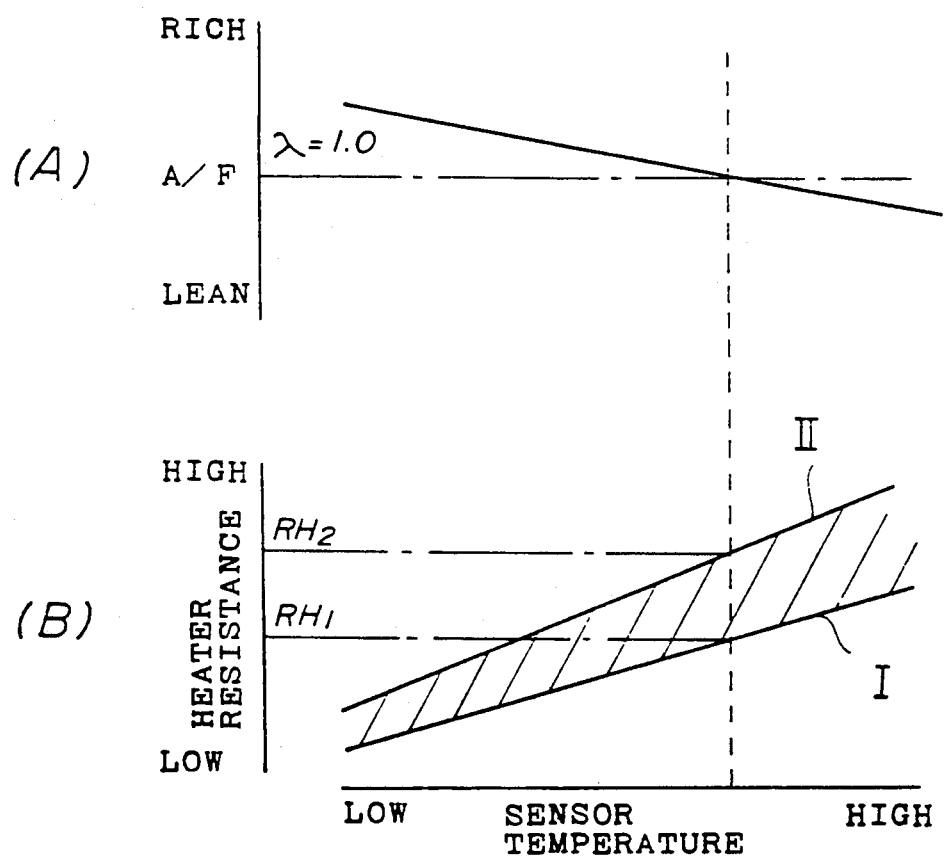
FIG. 1 is a graph showing relationships between variations in the heater resistance values of oxygen sensors and a stoichiometric air-fuel ratio.
Figure 11:
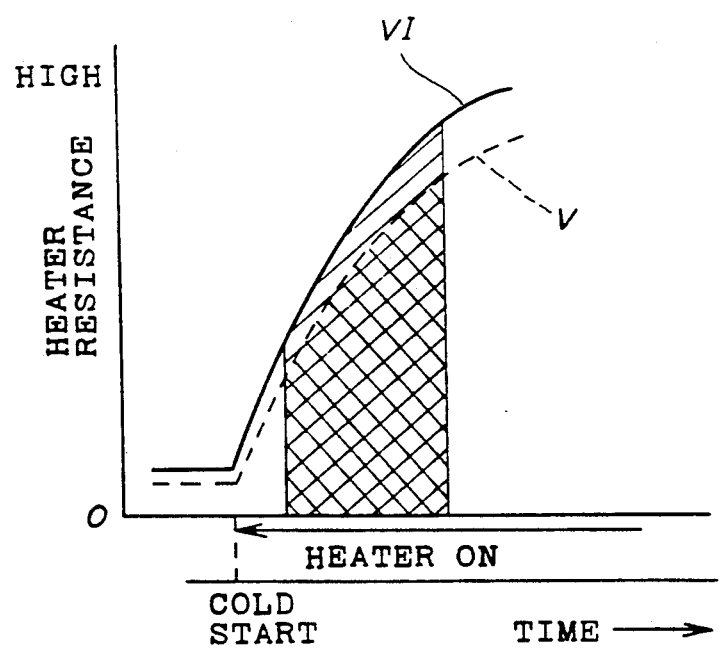
FIG. 11 is a graph showing a relationship between the heater resistance value and time during which a current is allowed to pass through the heater for the oxygen sensor.

Referring to FIG. 11, two oxygen sensors have different heater resistance characteristics indicated by V and VI. The heater resistance values of the two sensor heaters increase after the cold start. Energies corresponding to two areas respectively hatched are supplied to the heater 43a. Thus, it is possible to detect the difference between the heater resistance values of the two sensor heaters from the difference between these two areas. In other words, the areas change in accordance with the degrees of change in the resistance obtained when a certain power is respectively supplied to the oxygen sensors. Thus, the ratio RHN/PN corresponds to the degree of change in the resistance of the heater obtained when a certain power is supplied thereto. Thus, if the difference between the heater resistances of two oxygen sensors varies in accordance with the sensor temperature, as shown in FIG. 1, it is possible to definitely detect the above difference.

From the above point of view, it may be possible to obtain the target resistance value RT from the difference between the heater resistance values obtained by means of sampling carried out at predetermined intervals in the state where a certain power is supplied to the heater 43a. However, the heater resistance values RH detected immediately after the engine is started have errors because of great variations in the battery voltage. Thus, it is preferable to use the aforementioned procedure which is not affected by errors contained in the detected heater resistance values RH.

Figure 12:
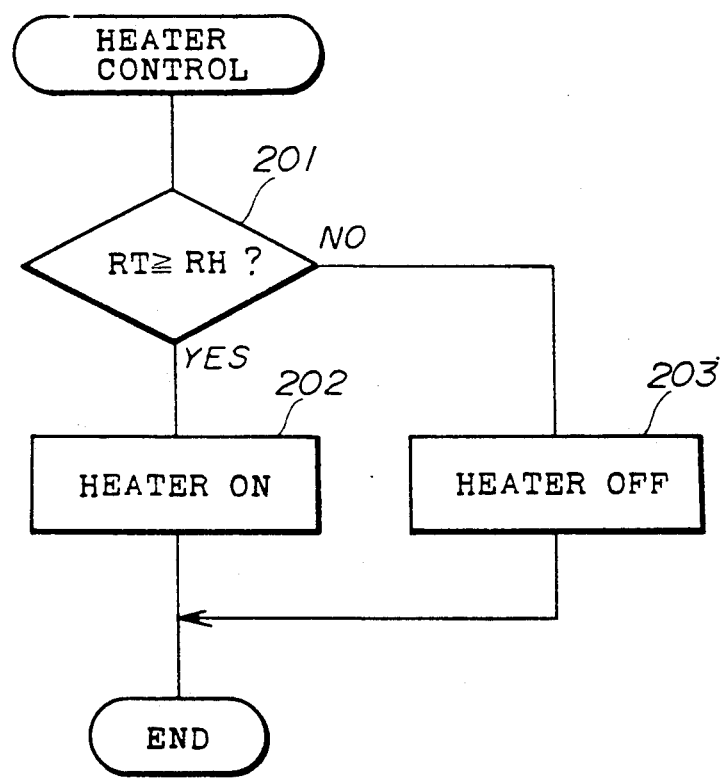
FIG. 12 is a flowchart of a heater control routine executed in the embodiment of the present invention.

A description will now be given of a control operation intended to control the heater resistance value RH at the target resistance value RT determined by the above-mentioned RT learning routine. FIG. 12 is a flowchart of a heater control routine which realizes the aforementioned power control unit 15 shown in FIG. 2 and which is executed every 65 milliseconds.

At step 201, the CPU 61 determines whether or not the target resistance value RT is equal to or greater than the heater resistance value RH. The heater resistance value RH is measured as follows. A high-level signal is applied to the base of the switching transistor 52 shown in FIG. 6 for the first few milliseconds of the above 65 ms period. In response to the high-level signal, the switching transistor 52 is turned ON, so that a current is allowed to pass through the heater 43a, the collector and emitter of the switching transistor 52, and the resistor 53. Then, the heater resistance value RH is calculated using the following formula:

$$RH = R_C[((V_B/V_C) - 1)] \tag{5}$$

where $V_B$ is the battery voltage, and $V_C$ is the voltage developed across the resistor $R_C$ having the known resistance value.

When the heater resistance value RH is equal to or smaller than the target resistance value RT, the CPU 61 executes step 202, at which step the heater 43a is turned ON and the procedure shown in FIG. 12 ends. Thus, when RT≧RH, the switching transistor 52 is continuously maintained in the ON state during the rest of the 65 ms period subsequent to the first few milliseconds. Thereby, the current continues to pass through the heater 43a, so that it is heated toward a higher temperature.

On the other hand, when the heater resistance value RH is larger than the target resistance value RT, the CPU 61 executes step 203 shown in FIG. 12, at which step the heater 43a is turned OFF. Then, the procedure shown in FIG. 12 ends. Thus, the switching transistor 52 is maintained in the OFF state during the rest of the 65 ms period following the aforementioned first few milliseconds, when RT<RH. Thereby, no current passes through the heater 43a, so that the temperature of the heater 43a decreases. In the above-mentioned way, the power supplied to the heater 43a is controlled so that the resistance RH of the heater 43a is always equal to the target resistance value RT, so that the heater 43a is maintained at a fixed temperature.

Figure 13:
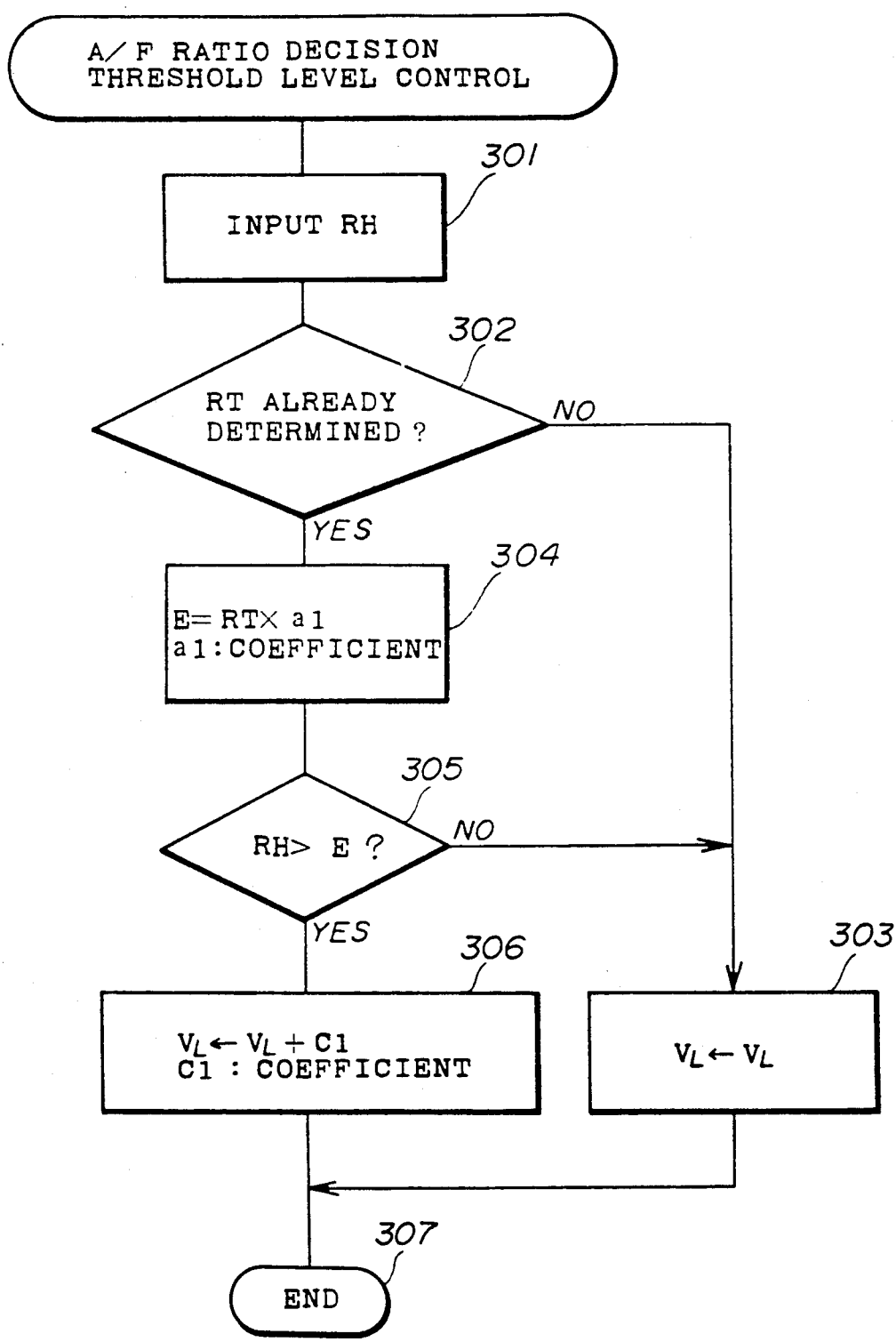
FIG. 13 is a flowchart showing a fuel control apparatus having the heater control apparatus according to the present invention.

A description will now be given of a fuel control apparatus using the heater resistance control device according to the present invention. FIG. 13 shows an air-fuel (A/F) ratio decision threshold level control routine, which is executed by the aforementioned microcomputer 21. As has been described previously, the titania sensor element has great temperature dependence, as shown in FIG. 5. The resistance of the titania sensor element decreases as the temperature increases.

Figure 14:
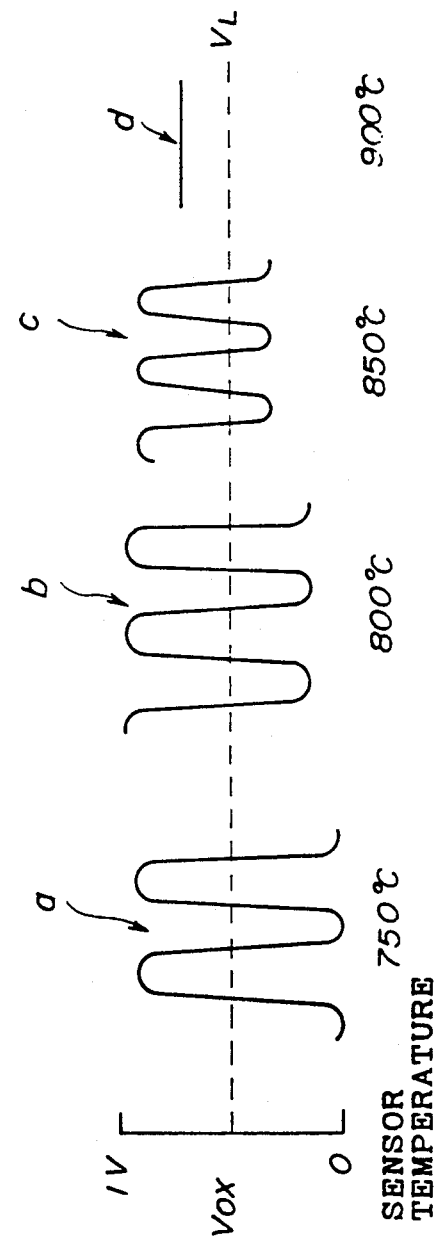
FIG. 14 is a waveform diagram showing a relationship between a signal output by the oxygen sensor and temperature of the oxygen sensor.

The low level of the output voltage $V_{OX}$ of the titania oxygen sensor obtained when the air-fuel ratio is lean, increases as the sensor temperature increases, because the resistance $R_t$ of titania (sensor resistance) decreases as the sensor temperature increases. As shown in FIG. 14, when the sensor temperature is 750° C., which is the target sensor temperature, the output voltage $V_{OX}$ has a, waveform 'a' which has a low level equal to 0 (V) obtained for a lean air-fuel ratio, and a high level equal to 1 (V) obtained for a rich air-fuel ratio. When the sensor temperature is equal to 800° C. and 850° C., the output voltage $V_{OX}$ of the titania oxygen sensor has waveforms 'b' and 'c', respectively. It can be seen from FIG. 14, the low level of the output voltage $V_{OX}$ obtained when the air-fuel ratio is lean increases as the temperature increases. When the sensor temperature is 900° C., the output voltage $V_{OX}$ obtained for the lean air-fuel ratio exceeds an A/F ratio decision threshold level $V_L$, as indicated by 'd' shown in FIG. 14. Thus, when the sensor temperature is high so that the low level of the output voltage $V_{OX}$ obtained for the lean air-fuel ratio is higher than the threshold voltage $V_L$, it is determined, on the basis of the output voltage $V_{OX}$, that the air-fuel ratio is rich. In this case, the air-fuel ratio is continuously controlled so that it is lean irrespective of the fact that the real air-fuel ratio is lean. Such a control scenario degrades drivability.

With the above in mind, the above-mentioned heater control is carried out for the titania oxygen sensor 43 so that the sensor temperature becomes equal to a target sensor temperature of, for example, 750° C. It will be noted that the exhaust gas temperature may be continuously high under certain traveling conditions where the vehicle is traveling on, for example, an upward slope. In this case, even if the heater control is operating for the titania oxygen sensor 43 and the power supply to the heater 43a is stopped, the sensor temperature may increase to 900° C.

The A/F ratio decision threshold level control routine shown in FIG. 13 is intended to eliminate the above-mentioned disadvantage. At step 301, the CPU 61 reads the heater resistance value RH calculated by the aforementioned formula (5) from the RAM 63, and inputs it thereto. At step 302, the CPU 61 determines whether or not the RT learning routine shown in FIG. 8 has been carried out. When it is determined, at step 302, that the RT learning routine has not yet been completed, the CPU 61 does not change the A/F ratio decision threshold level $V_L$ at step 303, and the procedure ends at step 307.

On the other hand, when it is determined, at step 302, that the target resistance value RT has been calculated based on the rate of change of the heater resistance value RH, at step 304 the CPU 61 calculates a threshold parameter (decision value) E by multiplying the target resistance value RT by a coefficient $a_1$. The coefficient $a_1$ is determined so that it can predict a sensor temperature at which the low level of the output voltage $V_{OX}$ of the oxygen sensor 43 obtained for the lean air-fuel ratio exceeds the A/F ratio decision threshold level $V_L$ (equal to, for 0.45 (V)) and the air-fuel ratio is continuously controlled to the lean value (this control is referred to as an F/B lean open control). When the F/B lean open control is executed at a temperature equal to or higher than 900° C., a predictive sensor temperature is set to, for example, 850° C.

On the other hand, the heater resistance value RH is expressed as follows:

$$RH = R_0(1 + aT) \quad (6)$$

where $R_0$ is a heater resistance value obtained at 0° C., $a$ is a coefficient (equal to 0.0033 when the heater 43a includes platinum), and T is the temperature (°C). Thus, the heater resistance $RH_{850}$ obtained when the sensor temperature is 850° C. is expressed as follows with respect to the target resistance value $RH_{750}$ (=RT) defined at a sensor temperature of 750° C.:

$$RH_{850} = [(1 + 0.0033 \times 850)/(1 + 0.0033 \times 750)]RT$$
$$= a_1 \times RT = E$$

where E is the threshold parameter. Thus, the coefficient $a_1$ is equal to 1.095.

At step 305 shown in FIG. 13, the CPU 61 determines whether or not the heater resistance value RH is larger than the above-mentioned threshold parameter E. When RH>E, at step 306 the CPU 61 adds the A/F ratio decision threshold level $V_L$ and a constant C1 (equal to, for example, 0.25 V), so that the A/F ratio decision threshold level $V_L$ is increased to a level at which the F/B lean open control does not take place. On the other hand, when RH≦E, the CPU 61 does not change the A/F ratio decision threshold level $V_L$ (step 303), and ends the routine shown in FIG. 13. In the above-mentioned way, it is possible to precisely detect the sensor temperature of the titania oxygen sensor 43 from the heater resistance RH and to prevent the occurrence of the F/B lean open control when the sensor temperature becomes equal to or higher than 900° C. As a result, it becomes possible to prevent the deterioration of drivability.

A description will now be given of another fuel control apparatus in which the aforementioned heater control is used for a decision regarding the execution of an OTP (over travel power) control. The OTP control is such that when the internal combustion engine 11 is working at a high load and/or a high rate of revolution which may damage structural parts of the exhaust system, the air-fuel ratio is made rich so that the amount of evaporative cooling of the fuel increases and thus the exhaust temperature decreases. The conditions for the execution of such an OTP control can be determined by studying the conditions where the structural elements of the exhaust system are excessively heated for a long period of time, and can be defined by a map (table) depending on the engine speed and the amount of intake air or the relationship between the engine speed and the opening angle of the throttle.

Even when the structural parts of the exhaust system are not actually heated excessively, the OTP control may be performed when the engine is overworking or working in a particular circumstance (a high ground or low temperature). In this case, the fuel economy and/or exhaust emissions may be degraded. When the condition defined when the OTP control executing condition is determined deteriorates with age, the OTP control may not be carried out correctly, so that the structural elements of the exhaust system may deteriorate.

Figure 15:
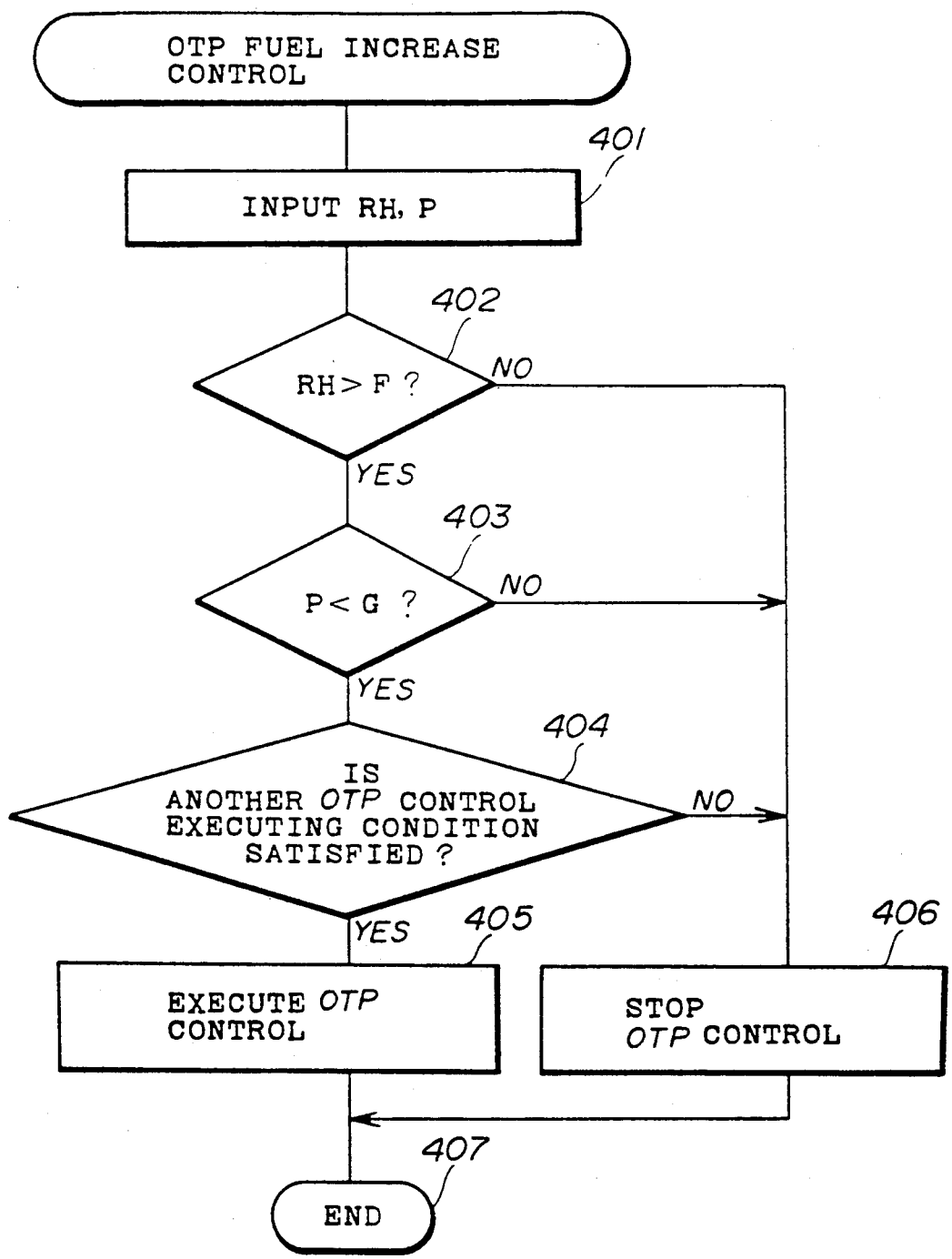
FIG. 15 is a flowchart showing a fuel control apparatus having the heater control apparatus according to the present invention.

FIG. 15 is a flowchart of an OTP control routine intended to eliminate the above-mentioned problems. At step 401, the CPU 61 reads out, from the RAM 63, the heater resistance value calculated by the aforementioned formula (5) and the amount of power supplied to the heater 43a calculated by the aforementioned formula (2). At step 402, the CPU 61 determines whether or not the heater resistance value RH is larger than a predetermined value F. When the result obtained at step 402 is YES, at step 403 the CPU 61 determines whether or not the amount of power read out at step 401 is greater than a predetermined value G.

The predetermined value F is equal to a value obtained by adding a predetermined value $\beta$ to the target resistance value RT obtained by the RT learning routine shown in FIG. 8. The predetermined value G is very close to zero. Thus, when it is determined, at the steps 402 and 403 that RH>F and P<G, the heater resistance value RH obtained, when the amount of power supplied to the heater 43a is almost zero, is larger than the target resistance value RT by $\beta$ or more. At this time, the CPU 61 determines that the temperature of the structural parts of the exhaust system has exceeded a critical temperature. That is, the state where the amount of power supplied to the heater 43a is almost zero can be recognized so that the oxygen sensor 43 is heated by only the thermal energy of the exhaust gas. The temperature obtained at this time is representative of the temperature of the exhaust gas. Further, the sensor temperature and the heater resistance value RH have a proportional relationship, so that the detection of the heater resistance RH corresponds to the detection of the sensor temperature. Furthermore, since the oxygen sensor 43 is exposed to the exhaust gas, the structural parts of the exhaust system will have the highest temperature among the other structural parts of the engine. For the above-mentioned reasons, it is possible to detect the representative temperature of the structural parts of the exhaust system from the heater resistance value RH obtained when the amount of power P supplied to the heater 43a is almost zero. In the above-mentioned way, the temperature of the exhaust system structural parts exceeds the critical temperature.

When RH>F or P<G, the CPU 61 executes step 404 at which step it is determined that another OTP control executing condition is satisfied. The OTP control executing condition decided at step 404 is determined on the basis of the engine speed and the amount of intake air or the relationship between the engine speed and the opening angle of the throttle in the same way as a conventional condition. When it is determined, at step 404, that the OTP control executing condition is satisfied, then at step 405 the CPU 61 executes the OTP control in which the amount of fuel is increased, and ends this routine. On the other hand, when either RH≦F or P≧G is satisfied, or when the result at step 404 is NO, the CPU 61 stops the OTP control at step 406, and ends this routine at step 407.

According to the control procedure shown in FIG. 15, the OTP control is not carried out when the engine is overworking or working under a particular condition. Thus, it is possible to improve the fuel economy and reduce impurities, such as CO, contained in the exhaust gas. Since it is not necessary to use a sensor exclusively for this task, such as an exhaust gas temperature sensor, it becomes possible to realize this simple and less expensive OTP control.

The present invention is not limited to the specifically disclosed embodiments, and variations and modifications may be made without departing from the scope of the present invention.

What is claimed is:

1. An apparatus for controlling a heater for an oxygen sensor, said apparatus comprising:
   heater resistance value detecting means for detecting a heater resistance value of said heater;
   power control means, operatively coupled to said heater and said heater resistance value detecting means, for controlling a power supplied to said heater so that the heater resistance value is equal to a target resistance value; and
   target resistance value setting means, operatively coupled to said heater resistance value detecting means and said power control means, for calculating a rate of change in the heater resistance value detected by said heater resistance value detecting means and for determining said target resistance value on the basis of the rate of change in the heater resistance value.

2. An apparatus as claimed in claim 1, wherein said target resistance value setting means comprises:
   first means for calculating an accumulated resistance value obtained by adding heater resistance values of said heater detected during a predetermined period;
   second means for calculating an average of power supplied to said heater during said predetermined period; and
   third means, operatively coupled to said first means and said second means, for calculating a ratio of said accumulated resistance value to said average of power corresponding to said rate of change in the heater resistance value of said heater.

3. An apparatus as claimed in claim 1, wherein:
   said target resistance value setting means comprises memory means for storing a plurality of target resistance values; and
   one of the plurality of target resistance values is read out from said memory means in accordance with the rate of change in the heater resistance value calculated by said target resistance value setting means.

4. An apparatus as claimed in claim 2, wherein
   said target resistance value setting means comprises memory means for storing a plurality of target resistance values; and
   one of the plurality of target resistance values is read out from said memory means in accordance with the ratio calculated by said third means.

5. An apparatus as claimed in claim 3, wherein said memory means stores the plurality of target resistance values which increase as the ratio calculated by said third means increases.

6. An apparatus as claimed in claim 2, wherein said said target resistance value setting means comprises counter means for measuring said predetermined period.

7. An apparatus as claimed in claim 1, wherein:
   said oxygen sensor is provided in an exhaust gas passage of an internal combustion engine; and
   said target resistance value setting means comprises means for discerning whether a coolant for cooling the internal combustion engine has a temperature within a predetermined temperature range and for activating said target resistance value setting means when it is discerned that the coolant has a temperature within said predetermined temperature range.

8. An apparatus as claimed in claim 1, wherein:
   said oxygen sensor is provided in an exhaust gas passage of an internal combustion engine,
   wherein said target resistance value setting means comprises:
   first means for determining whether or not the internal combustion engine is operating within a predetermined period after the internal combustion engine is started; and
   second means, operatively coupled to said first means, for making said target resistance value setting means inactive when it is determined that the internal combustion engine is operating within said predetermined period.

9. An apparatus as claimed in claim 1, wherein said power control means comprises:
   first means for determining whether or not said target resistance value is equal to or greater than the heater resistance value detected by said heater resistance value detecting means; and
   second means, operatively coupled to said heater and said first means, for supplying said heater with power during a predetermined time when said first means determines that said target resistance value is equal to or greater than said heater resistance value detected by said heater resistance value detecting means.

10. An apparatus as claimed in claim 9, wherein said power control means comprises third means, operatively coupled to said heater and said first means, for supplying said heater with no power during the predetermined time when said first means determines that said target resistance value is less than than said heater resistance value detected by said heater resistance value detecting means.

11. An apparatus as claimed in claim 1, wherein said heater resistance value detecting means comprises:
- a resistor connected to said heater in series, a series circuit composed of said heater and said resistor being coupled to a power source; and
- means for calculating said heater resistance value on the basis of a voltage drop developed across said resistor.

12. An apparatus as claimed in claim 1, wherein said oxygen sensor comprises a titania oxygen sensor.

13. An apparatus for controlling an amount of fuel supplied to an internal combustion engine on the basis of the concentration of oxygen contained in an exhaust gas of said internal combustion engine, said apparatus comprising:
- fuel injection means for injecting fuel into said internal combustion engine;
- an oxygen sensor for measuring the concentration of oxygen contained in the exhaust gas;
- a heater for heating said oxygen sensor; and
- control means, operatively coupled to said fuel injection means, for controlling the amount of fuel injected by said fuel injection means on the basis of the concentration of oxygen measured by said oxygen senor, wherein said control means comprises:
heater resistance value detecting means for detecting a heater resistance value of said heater;
power control means, operatively coupled to said heater and said heater resistance value detecting means, for controlling a power supplied to said heater so that the heater resistance value is equal to a target resistance value; and
target resistance value setting means, operatively coupled to said heater resistance value detecting means and said power control means, for calculating a rate of change in the heater resistance value of said heater measured by said heater resistance value detecting means and for determining said target resistance value on the basis of the rate of change in the heater resistance value, so that said oxygen sensor precisely measures the concentration of oxygen.

14. An apparatus as claimed in claim 13, wherein said control means comprises:
- correcting means, operatively coupled to said target resistance value setting means, for correcting said target resistance value in order to generate a decision value;
- decision means, operatively coupled to said heater resistance value detecting means and said correcting means, for determining whether or not the heater resistance value detected by said heater resistance value detecting means is greater than said decision value; and
- adjusting means, operatively coupled to said decision means, for controlling the amount of fuel so that it becomes more difficult for an air-fuel ratio to become lean than before when said decision means determines that the heater resistance value is greater than said decision value.

15. An apparatus as claimed in claim 14, wherein said correcting means comprises means for multiplying the target resistance value by a predetermined coefficient in order to generate said decision value.

16. An apparatus as claimed in claim 14, wherein said correcting means comprises means for adding a predetermined coefficient to the target resistance value in order to generate said decision value.

17. An apparatus as claimed in claim 14, wherein said adjusting means adjusts the amount of fuel so that it increases when said decision means determines that the heater resistance value is greater than said decision value.

* * * * *

UNITED STATES PATENT AND TRADEMARK OFFICE
CERTIFICATE OF CORRECTION

PATENT NO. : 5,111,792

DATED : May 12, 1992

INVENTOR(S) : Nagai et al.

It is certified that error appears in the above-identified patent and that said Letters Patent is hereby corrected as shown below:

On the title page, insert the following:

[30] Foreign Application Priority Data
June 11, 1990 [JP]   Japan..............2-151822
April 23, 1991 [JP]  Japan..............3-92298

<u>In the Abstract</u>
line 4, change "the" to --a--; same line, change "a" to --the--.

Column 1, line 20, change "in" to --of--.
          line 22, change "of" first occurrence to --in--.
          line 48, delete the comma.

Column 7, line 7, delete "learn-"
          line 8, delete "ing".

UNITED STATES PATENT AND TRADEMARK OFFICE
CERTIFICATE OF CORRECTION

PATENT NO. : 5,111,792
DATED : May 12, 1992
INVENTOR(S) : Nagai et al

It is certified that error appears in the above-indentified patent and that said Letters Patent is hereby corrected as shown below:

Column 10, line 46, delete the comma, (2nd occurrence)
           line 47, insert a comma after " 'a' ".

Signed and Sealed this

Fourteenth Day of June, 1994

Attest:

BRUCE LEHMAN

Attesting Officer     Commissioner of Patents and Trademarks